United States Patent
Watanabe et al.

(10) Patent No.: US 10,211,463 B2
(45) Date of Patent: Feb. 19, 2019

(54) CARBON MATERIAL, FUEL CELL, AND METHOD FOR PRODUCING CARBON MATERIAL

(71) Applicant: NISSHINBO HOLDINGS INC., Chuo-ku, Tokyo (JP)

(72) Inventors: Masayoshi Watanabe, Kanagawa (JP); Kaoru Dokko, Kanagawa (JP); Shiguo Zhang, Kanagawa (JP)

(73) Assignee: NISSHINBO HOLDINGS INC., Tokyo (JP)

( * ) Notice: Subject to any disclaimer, the term of this patent is extended or adjusted under 35 U.S.C. 154(b) by 761 days.

(21) Appl. No.: 14/834,082

(22) Filed: Aug. 24, 2015

(65) Prior Publication Data

US 2015/0364770 A1 Dec. 17, 2015

Related U.S. Application Data

(63) Continuation of application No. PCT/JP2014/053879, filed on Feb. 19, 2014.

(30) Foreign Application Priority Data

Feb. 27, 2013 (JP) .................... 2013-036840

(51) Int. Cl.
| | |
|---|---|
| *H01M 4/86* | (2006.01) |
| *C07D 471/22* | (2006.01) |
| *H01M 4/96* | (2006.01) |
| *H01G 11/24* | (2013.01) |
| *H01G 11/34* | (2013.01) |

(52) U.S. Cl.
CPC ........ *H01M 4/8663* (2013.01); *C07D 471/22* (2013.01); *H01G 11/24* (2013.01); *H01G 11/34* (2013.01); *H01M 4/96* (2013.01); *Y02E 60/13* (2013.01)

(58) Field of Classification Search
CPC .... H01M 4/8663; H01M 4/96; C07D 471/22; H01G 11/24; H01G 11/34
See application file for complete search history.

(56) References Cited

U.S. PATENT DOCUMENTS

| | | |
|---|---|---|
| 8,114,510 B2 | 2/2012 | Dai et al. |
| 8,513,319 B2 | 8/2013 | Dai et al. |
| 2011/0229401 A1 | 9/2011 | Dai et al. |

(Continued)

FOREIGN PATENT DOCUMENTS

| | | |
|---|---|---|
| JP | 2012101964 A | 5/2012 |
| JP | 2012527397 A | 11/2012 |

(Continued)

OTHER PUBLICATIONS

Haibo Wang, et al., "Review on Recent Progress in Nitrogen-Doped Graphene: Synthesis, Characterization, and Its Potential Applications", ACS Catalysis, vol. 2, Mar. 16, 2012, pp. 781-794.

(Continued)

*Primary Examiner* — Barbara L Gilliam
*Assistant Examiner* — Nathanael T Zemui
(74) *Attorney, Agent, or Firm* — Holtz, Holtz & Volek PC

(57) ABSTRACT

A carbon material according to an embodiment contains: 2% by mass or more and 15% by mass or less of nitrogen and 0.3% by mass or more and 2.5% by mass or less of sulfur, and 40% by mass or more of the nitrogen is a graphitic nitrogen.

5 Claims, 5 Drawing Sheets

(56) References Cited

U.S. PATENT DOCUMENTS

2013/0244862 A1    9/2013   Ivanovici et al.

FOREIGN PATENT DOCUMENTS

WO      2010135389 A2   11/2010
WO      2012070013 A1    5/2012

OTHER PUBLICATIONS

International Search Report (ISR) dated Apr. 22, 2014 issued in International Application No. PCT/JP2014/053879.
Paul H. Matter, et al. "Oxygen reduction reaction activity and surface properties of nanostructured nitrogen-containing carbon", Journal of Molecular Catalysis A: Chemical, vol. 264, Issues 1-2, Sep. 9, 2009, pp. 73-81.

CARBON MATERIAL, FUEL CELL, AND METHOD FOR PRODUCING CARBON MATERIAL

CROSS REFERENCE TO RELATED APPLICATION

This application is a continuation application of PCT/JP2014/053879 filed on Feb. 19, 2014 and claims the benefit of priority of the prior Japanese Patent Application No. 2013-036840, filed on Feb. 27, 2013, the entire contents of which are incorporated herein and in the appended claims and the accompanying drawings by reference.

BACKGROUND OF THE INVENTION

1. Field of the Invention

The present invention relates to a carbon material, a fuel cell containing the carbon material, and a method for producing the carbon material, and more particularly, it relates to a carbon material produced by heat treating a salt of an acid and an amine, the fuel cell containing the carbon material, and a method for producing the carbon material.

2. Description of the Related Art

A carbon material has a high electron conductivity and a low weight. Besides, a porous carbon material having a large surface area is now being examined for application to an electrode of a fuel cell, or the like. In particular, a nitrogen-containing carbon (N-doped carbon) has a high electron conductivity and shows graphite-like properties, and hence is attracting attentions.

International Publication No. 2010-135389 pamphlet (Japanese Patent Application Laid-Open Publication No. 2012-527397) discloses that a porous carbon material in the shape of a mold is produced by subjecting an ionic liquid, which has a strong interaction and high wettability with a material of the mold, to a carbonization treatment in a state filled in the material of the mold.

Besides, U.S. Patent Application Publication No. 2011/0229401 discloses that a nitrogen-containing carbon film having a high specific surface area is produced by subjecting, as a precursor, an aprotic ionic liquid containing nitrogen to a heat treatment under a non-oxidizing atmosphere. An aprotic ionic liquid containing nitrogen refers to an ionic liquid that does not have a hydrogen atom directly bonded to a nitrogen atom and in which a proton is not ionized.

SUMMARY OF THE INVENTION

A carbon material according to an embodiment contains 2% by mass or more and 15% by mass or less of nitrogen and 0.3% by mass or more and 2.5% by mass or less of sulfur, in which 40% by mass or more of the nitrogen is a graphitic nitrogen.

Besides, a method for producing a carbon material according to another embodiment includes: a salt synthesis step of synthesizing a protonic salt from sulfuric acid and a primary to tertiary amine: $NR^1R^2R^3$ (wherein at least one of $R^1$, $R^2$ and $R^3$ represents a hydrocarbon that may have a hetero atom with the remainder representing a hydrogen atom) having a C/N ratio of 1 or more; and a carbonization step of subjecting the protonic salt to a heat treatment at 600° C. or more and 1200° C. or less under an inert atmosphere.

DETAILED DESCRIPTION OF THE PREFERRED EMBODIMENTS

A carbon material according to an embodiment of the present invention is produced by a carbonization treatment of a protonic salt (a precursor) containing a nitrogen atom and easily synthesized through a reaction between a general and inexpensive (for example, $1/g or less) amine and sulfuric acid, and contains nitrogen and sulfur. A protonic salt containing a nitrogen atom refers to a salt that contains a hydrogen atom directly bonded to a nitrogen atom and releases (ionizes) a hydrogen atom as a proton.

As the amine, a primary to tertiary amine: $NR^1R^2R^3$ (wherein at least one of $R^1$, $R^2$ and $R^3$ represents a hydrocarbon that may contain a hetero atom with the remainder representing a hydrogen atom) having a C/N ratio (atomic ratio) of 1 or more is used. The amine may be any one of aliphatic amines, aromatic amines and heterocyclic amines as long as the amine is inexpensively and easily available. However, an amine not containing a carbon atom or a quaternary amine is not suitable. Besides, examples of a hetero atom that may be contained in the amine include S, O, F, Cl and P.

When sulfuric acid and an amine are mixed in a stoichiometric ratio to cause a neutralization reaction, a salt (a precursor) is synthesized. Sulfuric acid and an amine alone may be mixed, or a solvent may be used for the mixing. As the solvent, deionized water, methanol, ethanol, acetone or the like can be used depending upon the type of amine. This neutralization reaction is completed in an extremely short period of time.

The carbonization treatment is a heat treatment conducted under an inert atmosphere at 600° C. or more and 1200° C. or less. In the heat treatment, a temperature is increased to a prescribed temperature at a temperature increasing rate of 1 to 20° C./min, preferably a temperature increasing rate of 1 to 10° C./min, the prescribed temperature is retained for a prescribed period of time (of, for example, 0 to 3 hours), and then the temperature is lowered. The inert atmosphere is an Ar atmosphere, a nitrogen atmosphere or the like.

The carbon material of the present embodiment can be used as a catalyst support, an electrode material for energy conversion/storage, a conductive material, a hydrogen storage material, an adsorbent, a carbon dioxide selective adsorbent, a deodorant and the like.

Examples and Comparative Examples

Figure 1:
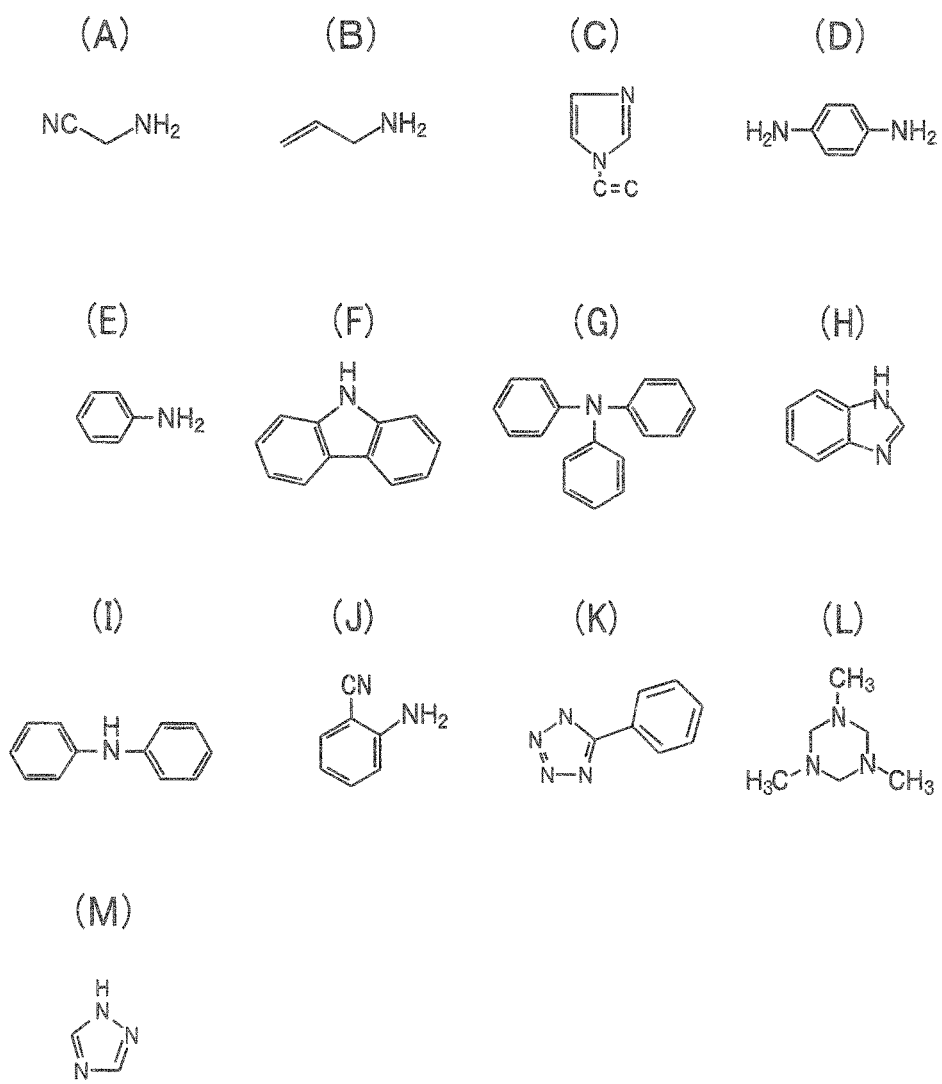
FIG. 1 is a diagram illustrating structures of amines used in production of a carbon material according to an embodiment.

FIG. 1 illustrates structures of the following amines used in methods for producing a carbon material of Examples and Comparative Examples.
(A) Cyanomethylamine: Aan
(B) Allylamine: Ally-NH2
(C) 1-Vinylimidazole: VIm
(D) p-Phenylenediamine: pPDA
(E) Aniline: phNH2
(F) Carbazole: Carbazole
(G) Triphenylamine: Tpa
(H) Benzimidazole: BeIm
(I) Diphenylamine: Dpa
(J) 2-Cyanoaniline: phCNNH2
(K) 5-Phenyltetrazole: 5-phtz
(L) Trimethyl hexahydrotriazine: Me3N3C3
(M) 1,2,4-Triazole: Triazole In the method for producing a carbon material of each Example, (a) sulfuric acid: $H_2SO_4$ was used as an acid, and for comparison, the following acids were also used:
(b) Trifluoromethanesulfonic acid: TfOH
(c) Nitric acid: $HNO_3$
(d) Dodecylbenzenesulfonic acid: C12phSO3H
(e) Bis(trifluoromethanesulfonyl)amide acid: HNTf2
(f) Hydrochloric acid: HCl <Salt Synthesis Step>

A protonic salt was synthesized by stoichiometrically neutralizing any one of the amines (A) to (M) and any one of the acids (a) to (f) under a nitrogen atmosphere for avoiding oxidation of the amine. Note that a part of a system was reacted in a solvent, followed by drying by a rotary evaporator and heating under vacuum at 80° C. for 24 hours for removing the solvent.

The thus synthesized salt was in the form of a liquid or a solid (powder).

<Carbonization Step>

Next, the synthesized salt (about 2 g) was heated in a tube furnace at a temperature increasing rate of 10° C./min under an Ar stream at 100 mL/min, and was retained at 1000° C. for 2 hours, and thus, a carbon material (Examples 1 to 12 and Comparative Examples 1 to 7) was obtained.

Incidentally, a salt synthesized from an amine not illustrated in FIG. 1 and sulfuric acid was also subjected, separately, to the salt synthesis/carbonization under the same conditions as in Examples to obtain a carbon material. Some of the salts were subjected to the carbonization step also at a low temperature (600° C. to 800° C.)

<Evaluation>

A yield of the carbon material was calculated by a gravimetric method. A nitrogen content (wt %) was measured by using a CHN elemental analysis device (Vario-ELIII). A composition (at %) and a chemical bonding state (a content of a graphitic nitrogen) were measured by using an X-ray electron spectroscopic apparatus (XPS) (PHI Quantera SXM).

Besides, a specific surface area (a BET value: $S_{BET}$) was calculated by measuring a nitrogen adsorption isotherm by using a nitrogen adsorption measuring device by a Brunauer-Emmett-Teller (BET) method.

<Evaluation Results>

The evaluation results of Examples and Comparative Examples are shown in Table 1.

TABLE 1

| | amine | | Acid | Salt | Yield (wt %) | N content (wt %) | content(XPS) (at %) | | | | Graphitic N | $S_{BET}$ ($m^2 \cdot g^{-1}$) |
|---|---|---|---|---|---|---|---|---|---|---|---|---|
| | | C/N | | | | | N | C | O | S | | |
| Example 1 | A Aan | 1.0 | a H2SO4 | Solid | 1.2 | 2.7 | 4.0 | 90.9 | 2.9 | 2.3 | 68 | 1380 |
| Example 2 | B Allyl-NH2 | 3.0 | a H2SO4 | Solid | 6.4 | 2.2 | 2.7 | 88.3 | 7.8 | 1.2 | 56 | 900 |
| Example 3 | C VIm | 2.5 | a H2SO4 | Solid | 5.4 | 3.4 | 4.0 | 87.6 | 7.6 | 0.8 | 63 | 937 |
| Example 4 | D pPDA | 3.0 | a H2SO4 | Solid | 18.6 | 5.0 | 4.9 | 91.4 | 2.8 | 1.0 | 50 | 644 |
| Example 5 | E phNH2 | 6.0 | a H2SO4 | Solid | 18.2 | 3.4 | 3.7 | 92.0 | 3.4 | 0.9 | 62 | 427 |
| Example 6 | F Carbazole | 12.0 | a H2SO4 | Solid | 44.8 | 3.2 | — | — | — | — | — | 222 |
| Example 7 | G Tpa | 18.0 | a H2SO4 | Solid | 44.0 | 2.7 | — | — | — | — | — | 236 |
| Example 8 | H BeIm | 3.5 | a H2SO4 | Solid | 16.9 | 5.9 | 4.7 | 89.2 | 5.6 | 0.5 | 70 | 168 |
| Example 9 | I Dpa | 12.0 | a H2SO4 | Solid | 46.0 | 4.5 | 4.9 | 87.8 | 6.8 | 0.6 | 65 | 242 |
| Example 10 | J phCNNH2 | 3.5 | a H2SO4 | Solid | 20.9 | 4.6 | 4.1 | 92.1 | 5.1 | 0.9 | 64 | 325 |
| Example 11 | K 5-phtz | 1.75 | a H2SO4 | Solid | 8.6 | 3.9 | 3.3 | 94.7 | 1.3 | 0.8 | 60 | 314 |
| Example 12 | L Me3N3C3 | 2.0 | a H2SO4 | Liquid | 4.1 | 3.8 | 3.3 | 91.7 | 3.7 | 1.3 | 60 | 875 |
| comparative example 1 | H BeIm | 4.0 | b TfOH | Solid | 18.5 | 7.7 | 6.7 | 87.5 | 5.4 | 0.4 | 61 | 54 |
| comparative example 2 | E phNH2 | 6.0 | c HNO3 | Solid | 13.3 | 3.5 | — | — | — | 0.0 | — | — |
| comparative example 3 | E phNH2 | 6.0 | d C12phSO3H | Solid | 6.9 | — | — | — | — | — | — | 3 |
| comparative example 4 | E phNH2 | 6.0 | e TfOH | Liquid | 9.7 | 4.5 | — | — | — | — | — | — |
| comparative example 5 | E phNH2 | 6.0 | f HNTf2 | Liquid | 8.9 | 3.5 | — | — | — | — | — | — |
| comparative example 6 | E phNH2 | 6.0 | g HCl | Solid | 0.0 | — | — | — | — | 0.0 | — | — |
| comparative example 7 | M Triazole | 0.67 | a H2SO4 | Solid | 0.0 | — | — | — | — | — | — | — |

As shown in Table 1, all of the carbon materials of the embodiment included 2% by mass or more and 15% by mass or less of nitrogen and 0.3% by mass or more and 2.5% by mass or less of sulfur. The carbon materials containing nitrogen in the above-described range exhibited a desired electrical conductivity, for example, an electrical conductivity of 500 S/m or more. The sulfur is a component derived from the sulfuric acid used in the salt synthesis, and conversely, the carbon material containing sulfur in the above-described range can be regarded to be produced with a sulfate used as a precursor.

The yield of the carbon material of Example 5, in which (a) sulfuric acid was used as the acid for the neutralization reaction with aniline was 18.2%. On the contrary, the yields of the carbon materials of Comparative Examples 2 to 7, in which (c) nitric acid, (d) dodecylbenzenesulfonic acid, (e) bis(trifluoromethanesulfonyl)amide acid, and (f) hydrochloric acid were respectively used as the acid for the neutralization reaction with aniline were 0 to 13.3%, which were lower than the yield of the carbon material of Example 5.

In other words, although a protonic salt is synthesized from an acid different from sulfuric acid and an amine, a yield attained in the carbonization treatment is higher in using sulfuric acid. The cause of the high yield is not clear, but it is presumed that a dehydration/carbonization action peculiar to sulfuric acid leads to an excellent result.

Note that a yield of the carbon material of Comparative Example 7 in which the amine had a C/N ratio less than 1 was 0%, namely, a carbon material could not be obtained although a sulfate was a precursor. On the contrary, if a C/N ratio of the amine was 1 or more, a carbon material could be obtained by the carbonization treatment. Besides, the yields of the carbon materials of Examples were liable to be higher as the C/N ratio of the amine was higher. In order to attain a yield of 10% or more, the C/N ratio of the amine is preferably 3 or more Next, with respect to a specific surface area (a BET value) of each carbon material, even if the same amine (benzimidazole) was used, the carbon material of Comparative Example 1 using trifluoromethanesulfonic acid as the acid had a BET value of 54 $m^2/g$, which was lower than a BET value of 168 $m^2/g$ of the carbon material of Example 8 using sulfuric acid. Besides, even if the same amine of aniline was used, the carbon material of Comparative Example 3 using dodecylbenzenesulfonic acid as the acid had a BET value of 3 $m^2/g$, which was lower than a BET value of 427 $m^2/g$ of the carbon material of Example 5 using sulfuric acid.

In other words, if sulfuric acid is used for the neutralization reaction of an amine, a carbon material having a high BET value can be produced in a high yield.

For example, the BET values of the carbon materials of Examples 1 to 12 using sulfuric acid for the salt synthesis were all 100 $m^2/g$ or more. In particular, if the amine was (A) cyanomethylamine, (B) allylamine, (C) vinylimidazole or (D) phenylenediamine (Examples 1 to 4), the BET values were all 500 $m^2/g$ or more.

Here, the protonic salt (the precursor) easily synthesized through the reaction between the amine and sulfuric acid is particularly preferably in the form of a solid. This is because, if the precursor is in the form of a liquid, such as an ionic liquid, heating irregularities easily occur in the carbonization treatment and hence it is not easy to synthesize a carbon material in a large amount efficiently. In other words, if the precursor is in the form of a liquid, the carbonization reaction easily proceeds in the vicinity of the liquid surface but the carbonization reaction is difficult to proceed in the vicinity of a bottom of the liquid. On the contrary, if the precursor is in the form of a solid, more specifically, a solid powder, uniform heating is easily performed even if a large amount of the precursor is simultaneously subjected to the carbonization treatment, and hence, a carbon material can be efficiently mass-produced.

For example, protonic salts produced from the following amines and sulfuric acid are in the form of a solid, and can be used for efficiently producing a carbon material by the carbonization treatment in the same manner as in the present embodiment.

1-(2-Cyanoethyl)-2-phenylimidazole (3-(2-phenyl-1H-imidazol-1-yl)propanenitrile)
Triphenylphosphine
1,2,4-Triazole
2,4,5,6-Tetraaminopyrimidine (pyrimidinetetramine)
3-Cyanopyridine
4-Cyanopyridine
2,2'-Bipyridine
1,10-Phenanthroline
1,3-Diphenylguanidine
2,4-Diamino-6-phenyl-1,3,5-triazine
DL-phenylalanine (2-amino-3-phenylpropanoic acid)
Tributylamine(N,N-dibutyl-1-butanamine)
2-Aminopyrazine
5-Aminotetrazole
Hexamethylenetetramine
Hexanydro-1,3,5-triphenyl-1,3,5-triazine
Pyrazine
1,1,3,3-Tetramethylguanidine On the contrary, protonic salts produced from the following amines and sulfuric acid were in the form of a liquid.
N-methyl pyrrole
Diallylmethylamine(methyldiallylamine)
Triallylamine(N,N-bis(prop-2-enyl)prop-2-en-1-amine)
1-Vinylimidazole (1-ethenylimidazole)
Diethylmethylamine
1-(2-Cyanoethyl)-2-methylimidazole (3-(2-methyl-1H-imidazol-1-yl)propanenitrile)
1,8-Diazabicyclo undec-7-ene (2,3,4,6,7,8,9,10-octahydropyrimido[1,2-a]azepine)
Pyridine
1-Methylimidazole In consideration of all these results, the carbon material of Example 4, produced by subjecting a protonic salt in the form of a solid powder synthesized from (D) phenylenediamine and (a) sulfuric acid is the most preferable carbon material of the present embodiment.

Figure 2:
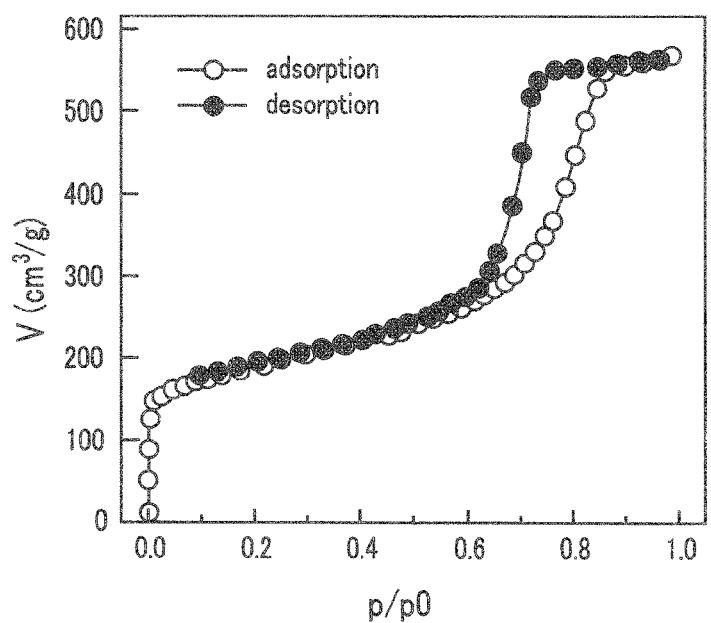
FIG. 2 is a diagram illustrating a nitrogen adsorption isotherm of a carbon material of the embodiment.
Figure 3:
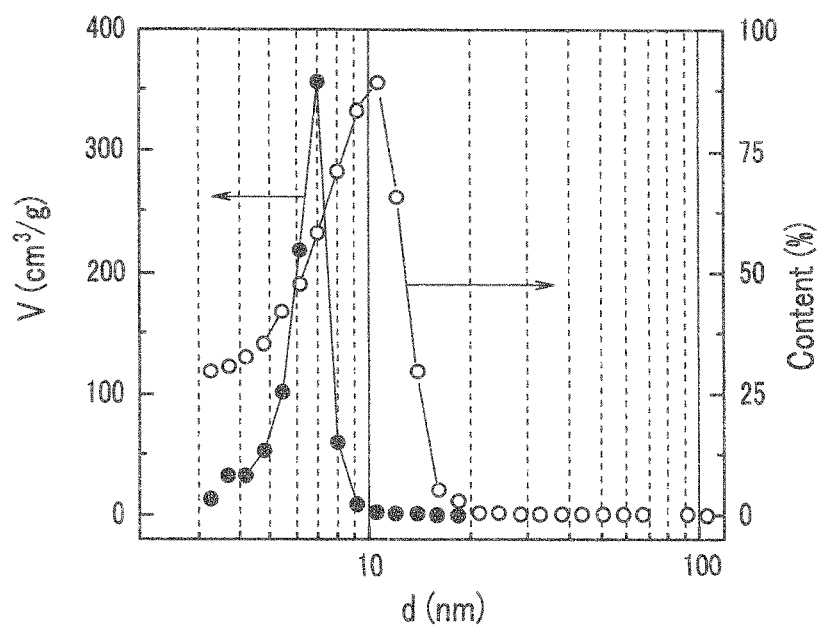
FIG. 3 is a diagram illustrating a pore size distribution of a carbon material of the embodiment.

Here, FIG. 2 illustrates an example of nitrogen adsorption isotherms of the carbon materials of Examples. Then, as illustrated in FIG. 3, the carbon material of Example 4 has, according to calculation from the nitrogen adsorption isotherm, a mesoporous structure having a peak value of pore sizes of 2 nm or more and 50 nm or less. Besides, all the carbon materials of the embodiment having a BET value of 100 $m^2/g$ or more were mesoporous carbon materials having a pore size distribution similar to that of Example 4.

As described later, a mesoporous carbon material has excellent characteristics as a catalyst support, an electrode material for energy conversion/storage, a conductive material, a hydrogen storage material, an adsorbent, a carbon dioxide selective adsorbent, a deodorant and the like.

Figure 4:
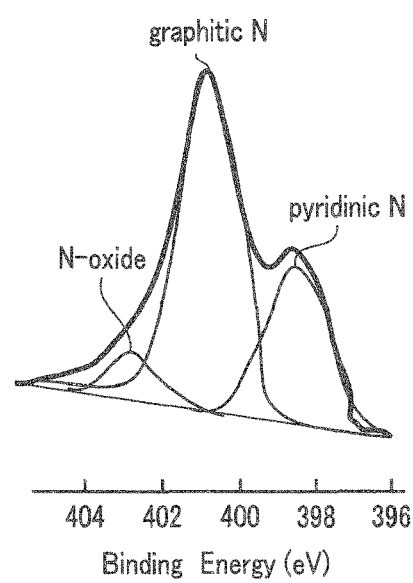
FIG. 4 is a diagram illustrating results of XPS analysis of the carbon material of the embodiment.
Figure 5:
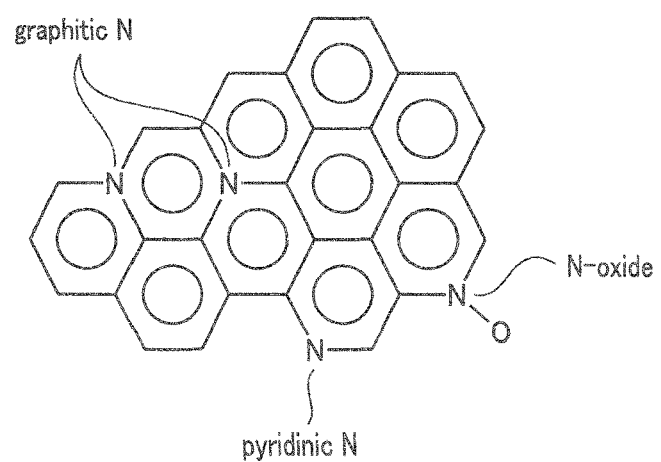
FIG. 5 is a diagram illustrating a structure of the carbon material of the embodiment.

Here, as illustrated in FIGS. 4 and 5, the carbon material 1 of Example 4 contained three types of nitrogens (a graphitic nitrogen, a pyridinic nitrogen and a nitrogen oxide) respectively having different chemical bonding states. Note that a ratio of the graphitic nitrogen in the nitrogen is preferably 40 at % or more because the graphitic nitrogen is involved in electrical conduction. If the ratio falls in the aforementioned range, a conductivity of, for example, 500 S/m or more is assured. Note that the upper limit of the ratio of the graphitic nitrogen is, for example, 90 at % in the carbon material of the present embodiment because of technical limits.

Incidentally, a carbon material resulting from the carbonization can be further subjected to an activation treatment with an alkaline solution for increasing the BET value. The activation treatment refers to a treatment for immersing a carbon material in a strong alkaline solution, such as 5 M/L to 20 M/L of NaOH or KOH, at 50° C. or more and 100° C. or less for 10 minutes or more and 3 hours or less.

Figure 6:
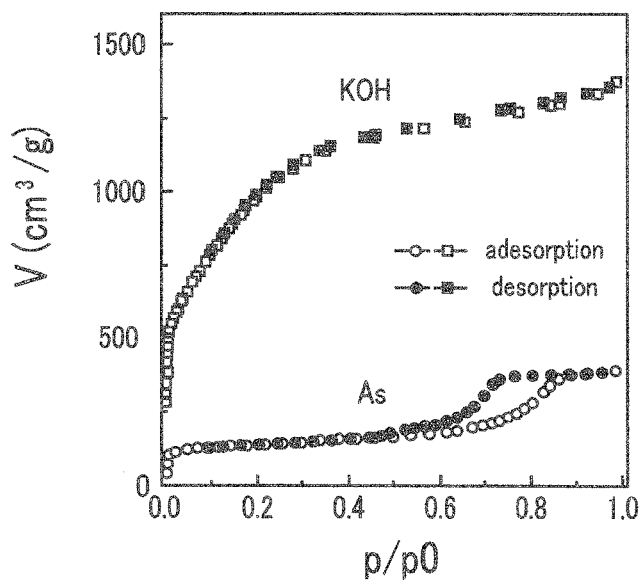
FIG. 6 is a diagram illustrating nitrogen adsorption isotherms, obtained before and after a sodium hydroxide treatment, of a carbon material of the embodiment.

For example, as illustrated in FIG. 6, a carbon material (As) of Example 6A obtained by subjecting the same salt as that used for the carbon material of Example 6 to the carbonization treatment at 800° C. attained a BET value of 3573 m$^2$/g when immersed in a 10 M/L KOH aqueous solution at 80° C. for 1 hour (KOH). Incidentally, if the activation treatment is performed, a BET value is more easily increased by performing the carbonization treatment at a temperature lower than that of the activation treatment, for example, at 600° C. or more and 900° C. or less.

<Application of Carbon Material>

The nitrogen-containing carbon material of the present embodiment is a mesoporous conductive material, and hence can be used as an electrode of a fuel cell.

For use as an electrode material or the like, a carbon material in the form of a powder is compression molded together with, for example, a PEFT powder.

Figure 7:
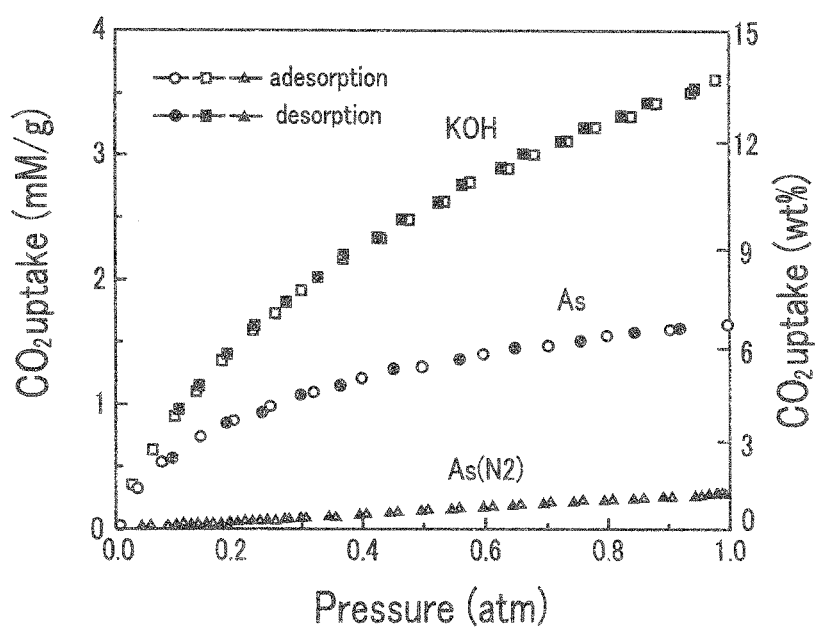
FIG. 7 is a diagram illustrating carbon dioxide adsorption/desorption, obtained before and after the sodium hydroxide treatment, of the carbon material of the embodiment.

As illustrated in FIG. 7, the carbon material (As: before subjecting to the alkali treatment) of Example 6 (adsorbs/desorbs) 1.6 mM/g of carbon dioxide, but an amount of (adsorbed/desorbed) nitrogen (As (N2)) is merely 0.2 mM/g. Therefore, a carbon dioxide adsorbing device using the carbon material of Example 6A as an adsorbent can selectively recover carbon dioxide discharged from, for example, a plant.

Besides, as illustrated in FIG. 7, the carbon material (KOH) of Example 6A increased in the specific surface area by the alkali treatment (adsorbed/desorbed) 3.57 mM/L of carbon dioxide.

Note that the carbon materials of Examples 1, 3 and 12 respectively (adsorb/desorb) 1.63 mM/g, 2.58 mM/g and 2.44 mM/g of carbon dioxide.

Incidentally, when a carbon material having substantially the same structure as the carbon material of Example 6 but not containing nitrogen was evaluated for comparison, an amount of adsorbed carbon dioxide was much smaller than that of the carbon material of Example 6. This revealed that it is extremely significant for a carbon material to be used as a carbon dioxide adsorbent to contain 2% by mass or more of nitrogen.

Figure 8:
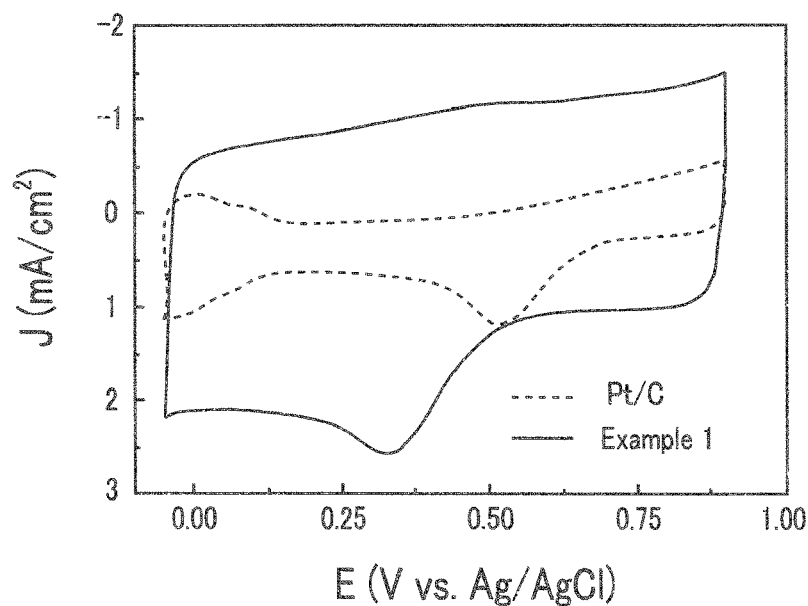
FIG. 8 is a diagram illustrating an oxygen reduction catalyst characteristic (CV) of a carbon material of the embodiment.
Figure 9:
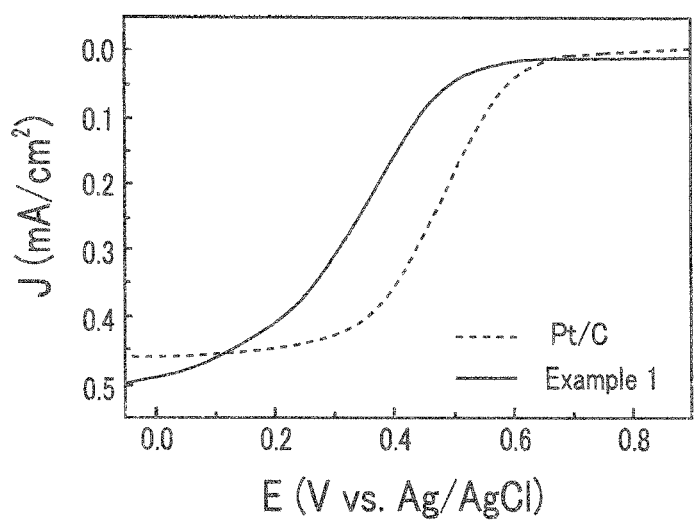
FIG. 9 is a diagram illustrating an oxygen reduction catalyst characteristic (RDE) of the carbon material of the embodiment.

Besides, FIG. 8 illustrates polarization curves (CV: 100 mV/s), obtained by using a general electrochemical cell, of a carbon material electrode of Example 1 and a generally used Pt/C electrode in an acidic solution (a 0.5 M sulfuric acid aqueous solution), and FIG. 9 illustrates stationary polarization curves (10 mV/s) obtained by using a rotary electrode device (RDE, rotational speed: 1600 rpm).

In both the polarization curve of the Pt/C electrode (platinum-supporting carbon electrode) shown with a broken line in FIG. 8 and the polarization curve of the carbon material electrode of Example 1 shown with a solid line, peaks derived from an oxygen reduction reaction can be observed. Since the carbon material electrode of Example 1 has a larger specific surface area than the Pt/C electrode, a current is larger.

On the other hand, in the stationary polarization curves illustrated in FIG. 9, the oxygen reduction reaction proceeds from a higher potential in the Pt/C electrode. On the contrary, the carbon material electrode of Example 1 also shows a comparatively good oxygen reduction activity. Incidentally, since the carbon of the carbon material electrode of Example 1 contains no transition metal ions, the oxygen reduction catalyst activity is an original physical property of the carbon material.

In other words, the carbon material of Example 1 shows an oxygen reduction catalytic activity substantially equivalent to that of an expensive Pt electrode.

Accordingly, the carbon material of Example can be suitably used as a fuel cell using an acidic electrolyte.

What is claimed is:

1. A method for producing a carbon material, comprising:
   a salt synthesis step of synthesizing a protonic salt from sulfuric acid and a primary to tertiary amine: NR$^1$R$^2$R$^3$ wherein at least one of R$^1$, R$^2$ and R$^3$ represents a hydrocarbon that may have a hetero atom with the remainder representing a hydrogen atom and wherein the primary to tertiary amine has a C/N ratio of 1 or more; and
   a carbonization step of subjecting the protonic salt to a heat treatment at 600° C. or more and 1200° C. or less under an inert atmosphere.

2. The method for producing a carbon material according to claim 1, wherein the salt is in the form of a solid.

3. The method for producing a carbon material according to claim 1, further comprising, after the carbonization step, an alkaline solution immersion step.

4. The method for producing a carbon material according to claim 1, wherein the amine is cyanomethylamine, allylamine, vinylimidazole or phenylenediamine.

5. The method for producing a carbon material according to claim 4, wherein the amine is phenylenediamine, and a specific surface area of the carbon material is 500 m$^2$/g or more.

* * * * *